United States Patent [19]

Abblard et al.

[11] 4,041,109

[45] Aug. 9, 1977

[54] DIPHOSPHOROUS

[75] Inventors: Jean Abblard, St. Didier au Mont d'Or; Georges Marmain, Fontaine sur Seine; Andrée Viricel, Lyon, all of France

[73] Assignee: Philagro, France

[21] Appl. No.: 561,220

[22] Filed: Mar. 24, 1975

[30] Foreign Application Priority Data

Mar. 22, 1974 France .............................. 74.10988

[51] Int. Cl.$^2$ ........................... C07F 9/21; A01N 9/36
[52] U.S. Cl. .................................. 260/927 R; 424/209
[58] Field of Search .................................. 260/927 R

[56] References Cited

U.S. PATENT DOCUMENTS

| 3,152,164 | 10/1964 | Oswald | 260/927 R |
| 3,626,039 | 12/1971 | Hoffmann | 260/927 R X |
| 3,702,878 | 11/1972 | Saito | 260/927 R |

OTHER PUBLICATIONS

Oswald, "Candian Journal of Chemistry," vol. 37, (1959), pp. 1498–1504.

*Primary Examiner*—Anton H. Sutto
*Attorney, Agent, or Firm*—Robert E. Burns; Emmanuel J. Lobato; Bruce L. Adams

[57] ABSTRACT

New cyclic diphosphorous compounds are disclosed together with fungicidal compositions containing same useful in a process for controlling fungal plant infestations.

3 Claims, No Drawings

DIPHOSPHOROUS

FIELD OF INVENTION

This invention relates to new cyclic diphosphorous compounds.

THE INVENTION

The invention relates to novel cyclic diphosphorous compounds which are suitable for use in controlling fungus disease in plants and which correspond to either of the following formulae:

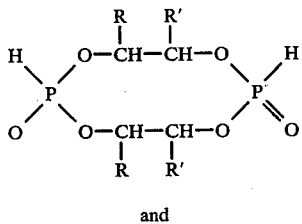

(I)

and

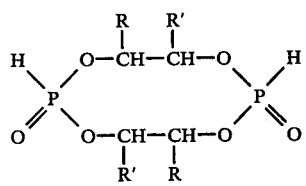

(II)

in which:

R and R', which may be the same or different, represent a hydrogen atom or an optionally halogenated alkyl radical containing from 1 to 5 carbon atoms; R and R' cannot simultaneously represent hydrogen.

Finally, the invention relates to fungicidal compositions which are suitable for use in controlling fungus disease in plants and which contain, as active material, at least one of the compounds of formula (I) or (II) above in which R and R', which may be the same or different, represent a hydrogen atom or an optionally halogenated alkyl radical containing from 1 to 5 carbon atoms;

DETAILED DESCRIPTION OF THE INVENTION

These compounds, of which only the most simple (R = R' = H) is known, may be prepared by various methods.

The first of these methods comprises reacting an anhydrous α-glycol with anhydrous phosphorus trichloride in solution in dichloromethane to form a cyclic glycol chlorophosphite in accordance with the following scheme:

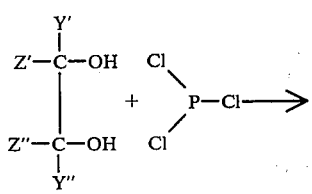

-continued

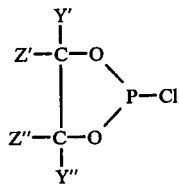

Since the reaction is highly exothermic, the reaction mixture has to be cooled. After about 1.5 hours, the solvent is removed by distillation, and the resulting product is subsequently distilled under reduced pressure.

The chlorophosphite in solution in dioxane is hydrolysed by the addition of water in accordance with the following reaction scheme:

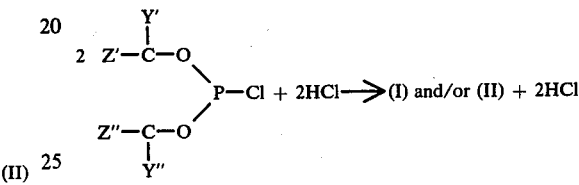

The release of hydrochloric acid is promoted by maintaining a temperature around ambient temperature and a reduced pressure.

It has been possible by this method to obtain compounds of formulae I and II in which R is the methyl radical and R' a hydrogen atom. Under the test conditions, a mixture of approximately 85% of these products is obtained, the balance being formed by 2-hydroxy-4-methyl-1,3,2-dioxaphospholane. The constituents of the mixture were characterised and their respective proportions determined by NMR-spectrography.

In a second method, an α-glycol is reacted with phosphorus trichloride in the presence of a low molecular weight alcohol (AOH) in accordance with the following scheme:

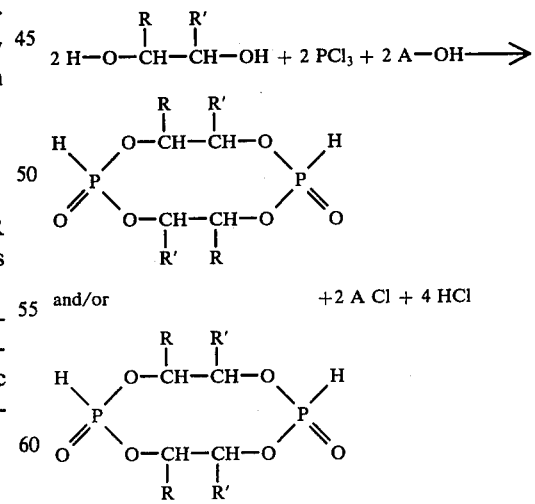

2,7-Dihydro-2,7-dioxo-1,3,6,8,2,7-tetraoxadiphosphadecane (compound 1), corresponding to the case where R = R' = H, was prepared by this method.

68.8 g (0.5 mol) of phosphorus trichloride are introduced with stirring over a period of 30 minutes into a mixture of 31 g (0.5 mol) of ethylene glycol and 16 g (0.5 mol) of methanol.

The mixture is left standing for 1 hour to return to ambient temperature. The remaining traces of methylene chloride and hydrochloric acid are then removed by stirring the mixture under reduced pressure. 54 g, i.e. a quantitative yield of 0.25 mol of a liquid with the following characteristics are obtained:

$n_D^{20}$: 1.485 b.p.: 97° C/0.25 mm Hg

This structure is confirmed by nuclear magnetic resonance (NMR) spectrography. The spectrums were formed at 60 mc/s in DMSO containing hexadeuterium with tetramethyl silane as internal reference. The identification of the protons is represented by the field displacement δ in units of ppm.

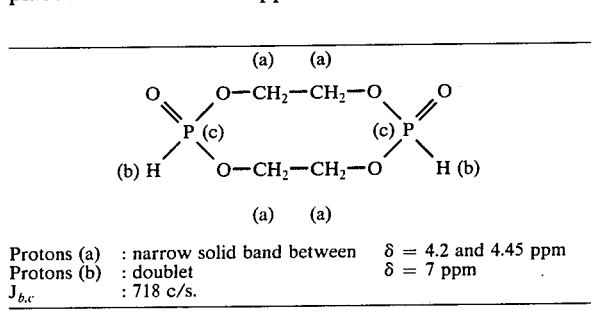

| Protons (a) | : narrow solid band between | δ = 4.2 and 4.45 ppm |
|---|---|---|
| Protons (b) | : doublet | δ = 7 ppm |
| $J_{b,c}$ | : 718 c/s. | |

2,7-Dihydro-2,7-dioxo-4,10-dimethyl-1,3,6,8,2,7-tetraoxadiphosphadecane and 2,7-dihydro-2,7-dioxo-4,9-dimethyl-1,3,6,8,2,7-tetraoxadiphosphadecane are obtained by the same method from 1,2-propane diol, phosphorus trichloride and methanol. A mixture of the two isomers (compound 2) is obtained in a yield of 90%: $n_D^{20}$: 1.469 b.p.: 76° C/0.025 mm Hg Other compounds of the same family can be obtained by this method, more especially compounds in which R = CH$_2$Cl R' = H (compound 3)
R = R' = CH$_3$ (compound 4).

A process similar to the process described above comprises reacting a cyclic glycol chlorophosphite with a lower alcohol, such as methanol, in methylene chloride under otherwise the same conditions.

In a third method described by Oswald (Can. J. Chem., vol. 37, 1959), transesterification is carried out by mixing α-glycol with a dialkyl phosphite in equimolar proportions.

In the case of ethylene glycol and diethyl phosphite, the mixture is heated to 130° – 140° C under a pressure of 120 to 150 mm Hg. On completion of the elimination of ethanol, the reaction product is fractionated under reduced pressure. Compound 1 is obtained in a yield of 56% in accordance with the following reaction scheme:

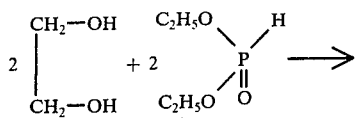

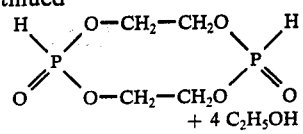

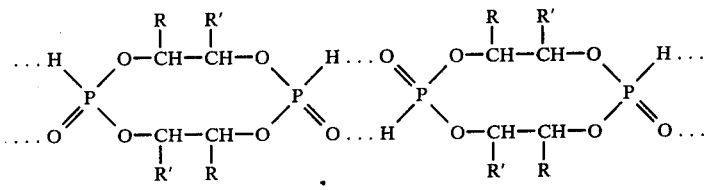

+ 4 C$_2$H$_5$OH

The cyclic compounds obtained by these methods have the property of becoming more viscous during storage, which may be explained by an association of the molecules through hydrogen bonding of the type:

[structure diagram]

These bonds are broken when the product is distilled so that the distillate, which is fluid, becomes viscous again after a few hours.

In addition, these compounds, irrespective of their presentation, can be hydrolysed to give compounds which are themselves fungicidal, such as optionally substituted mono-2-hydroxy ethyl phosphonates or their salts (cf. French Patent Application 73-37.994, and phosphorous acid and its salts (cf. French Patent Application No. 73-43.081).

It has been found that the compounds according to the invention show remarkable fungicidal properties, as demonstrated in the following Examples:

EXAMPLE 1

In vitro test on mycelian growth

The products according to the invention were tested for their action on the mycelian growth of the following fungi:

Rhizoctonia solani, responsible for canker of the neck,
Fusarium oxysporum, responsible for tracheomycosis,
Fusarium nivale, responsible for the damping off of seedlings of cereal crops,
Fusarium roseum responsible for fusariosis in cereal crops,
Sclerotinia minor, responsible for sclerotiniosis,
Sclerotinia sclerotiorum, responsible for sclerotiniosis,
Pythium de Baryanum, responsible for the damping off of seedlings,
Phomopsis viticola, responsible for excoriosis,
Septoria nodorum, responsible for septoriosis in cereal crops,
Helminthosporium, responsible for helminthosporiosis,
Verticillium, responsible for verticilliosis,
Cercospora beticola, responsible for cercosporiosis.

The so-called Agar Plate dilution method was used for each test. A mixture of gelose and an acetone solution or a wettable powder containing the active material to be tested in a concentration of 0.25 g/l, is introduced into a Petri dish at a temperature of approximately 50° C.

The wettable powder is prepared by mixing the following ingredients for 1 minutes in a blade mill:

| active material to be tested | 20 % |
|---|---|
| deflocculant (calcium lignosulphate) | 5 % |

-continued

| | |
|---|---|
| wetting agent (sodium alkyl aryl sulphate) | 1 % |
| filler (aluminium silicate) | 74 % |

This wettable powder is then mixed with a quantity of water sufficient for one application in the required dose.

The gelose-containing mixture is left to harden and mycelian culture discs of the fungus are placed on it.

A Petri dish similar to the first, but in which the gelose-containing medium does not contain any active material, is used as control.

After 4 days at 20° C, the surface area of the inhibition zone observed is evaluated and expressed as a percentage of the inoculated surface.

| Fungus | % inhibition Product No. 2 |
|---|---|
| Rhizoctonia | 50 |
| Fusarium oxysporum | 60 |
| Fusarium nivale | 65 |
| Fusarium roseum | 70 |
| Sclerotinia minor | 100 |
| Sclerotinia sclerotiorum | 50 |
| Pythium | 100 |
| Phomopsis | 50 |
| Septoria | 70 |
| Helminthosporium | 70 |
| Verticillium | 100 |
| Cercospora | 90 |

EXAMPLE 2

In vivo test on living organs:
Test on tomato mildew (*Phytophora infestans*)

One drop of a mixture of a suspension of spores containing approximately 80,000 units per cc and a suspension, in the required dilution, of a wettable powder with the same composition formulation as the wettable powder described in Example 1, in the case of an insoluble product, or in an acetone solution, is applied by spraying and/or dipping to freshly cut tomato leaves.

Under these conditions, product 2 affords complete protection in a dose of 0.5 g/l.

EXAMPLE 3

In vivo test on *Plasmopara viticola* in plants a. preventive treatment

Using a spray gun, the leaves of pot-grown grape vine plants (Gamay variety) are sprayed until uniformity wetted underneath with an aqueous suspension of a wettable powder with the following composition (by weight):

| | |
|---|---|
| active material to be tested | 20 % |
| deflocculant (calcium lignosulphate) | 5 % |
| wetting agent (sodium alkyl aryl sulphonate) | 1 % |
| filler (aluminium silicate) | 74 % | in the required dilution containing the active material to be tested in the dose in question. Each test was repeated twice.

After 48 hours, the plants are contaminated by spraying their leaves underneath with an aqeuous suspension containing approximately 80,000 units/cc of spores of the fungus.

The pots are then placed for 48 hours in an incubation cell at 20° C/100% relative humidity.

The plants are inspected 9 days after infestation.

Under these conditions, compounds 1 to 4 afford complete protection in a dose of 0.5 g/l.

In addition, it is pointed out that none of the products tested showed the least sign of phytotoxicity.

b. treatment after contamination

The procedure is as described in paragraph a) above, except that the plants are first contaminated and then treated with the active material to be tested, being inspected 9 days after contamination.

Under these conditions, compounds 1, 2 and 3, in a dose of 1 g/l, completely stop development of the mildew on the vine plants.

c. systemic test by root absorption

Several vine stocks (Gamay variety), each accommodated in a container filled with vermiculite and a nutritive solution, are sprayed with 40 cc of a solution containing 0.5 g/l of the material to be tested. After 2 days, the vine is contaminated with an aqueous suspension containing 100,000 spores/cc of *Plasmopara viticola*. This is followed by incubation for 48 days in a room at 20° C/100% relative humidity. The degree of infestation is assessed after about 9 days by comparison with an infested control which had been sprayed with 40 cc of distilled water.

Under these conditions, compounds 1, 2, 3 and 4, absorbed by the roots, afford complete protection to the vine leaves against the mildew, which clearly demonstrates the systemic nature of these compounds.

EXAMPLE 4

Systemic test by leaf absorption on mildew of the vine

Vine stocks (Gamay variety), each accommodated in a container filled with a mixture of clean soil and sand, are treated at the 7-leaf stage.

Treatment is carried out by spraying the underneaths of the lowest 4 leaves with a wettable powder containing 2.5 g/l of the active material to be tested.

After 2 days, the vine is contaminated with an aqueous suspension containing approximately 100,000 spores/cc of *Plasmopara viticola*. This is followed by incubation for 48 hours in a room at 20° C/100% relative humidity. The degree of infestation is assessed after about 9 days from the fifth to seventh highest leaves by comparison with a control which had been treated with distilled water.

Under these conditions, compounds 1, 2 and 3 afford complete protection to the upper leaves of the vine against mildew.

EXAMPLE 5

Open-air test on mildew of the vine

Groups of vine stocks (Gamay) are naturally infested at the beginning of August after abundant rainfall and frequent watering. These groups of vine stocks are then treated after 8, 14 and 23 days, respectively, with sprays of 50% of wettable powders respectively containing, as active material, compound no. 1, manganese ethylene-1,2-bis-dithiocarbamate (Manebe) and a mixture of these two compounds.

The following Table shows the results of inspections made 2, 8, 20, 35 and 45 days, respectively, after the last treatment. The results are expressed as percentage protection in relation to a contaminated, but untreated control.

| Active Material | dose g/l | Observation after | | | | |
|---|---|---|---|---|---|---|
| | | 2 days | 8 days | 20 days | 35 days | 45 days |
| compound No. 1 | 2 | 100 | 70 | 15 | 10 | 0 |
| manebe | 1.2 | 95 | 93 | 88 | 77 | 70 |
| compound No. 1 + manebe | 2 + 1.2 | 100 | 100 | 100 | 95 | 90 |

This Table clearly demonstrates firstly the excellent, immediate effect of compound No. 1, secondly the remarkable persistence of the mixture, which is greater than that of manebe used on its own, and finally the observed lack of any phytotoxicity of compound No. 1 alone or in combination on grape vines.

EXAMPLE 6

Test on tobacco

Plots of 5 tobacco plants (PB 91) are treated on the 15th June with a wettable powder containing an active material which, in one case, consists of 80% of manebe in a quantity of 160 g/l, and in another case of 50% of compound No. 2 in a quantity of 200 g/l. 1 plot is left untreated as control.

After 48 hours, the active materials plants are artificially contaminated (with *Peronospora tabacina*) and them fumigated. The treatment is then repeated once weekly.

An inspection is made on the 12th August by counting the number of patches of mildew per plot. The results are set out in the following Table:

| Product | Number of patches per plot |
|---|---|
| Control | 48 |
| Manebe | 4 |
| Compound 2 | 2 |

Other tests have shown that the compound according to the invention is also active against this mildew in curative treatment, and has a systemic action.

EXAMPLE 7

Avocado test

Young avocado plants (*Persea indicia*) are planted in soil infested with *Phytophtora cinnamomi*, after which the soil is sprayed with a solution containing 3 g/l of compound No. 2. A few plants are left untreated as controls. Under these conditions, the roots of the controls are completely destroyed after 20 days, whilst 90% of the roots of the treated plants are healthy.

EXAMPLE 8

Pineapple test

Pineapple plants are contaminated with *Phytophtora parasitica* and then treated after 48 hours by spraying with a solution containing 0.5 g/l of compound No. 2. After 30 days, the fungus has been completely inhibited in the treated plants, whereas the controls are infested.

EXAMPLE 9

Strawberry test

Ten strawberry plants (Surprise des Halles variety) are treated by soaking for 1 hour in an aqueous solution containing 0.2% of compound 2, dried and planted out on the June 14 in soil contaminated artifically with *Phytophtora cactorum*. Immediately afterwards and then once every 8 days until the July 18, the plants are sprayed with the same solution, which corresponds to a total application of 0.5 g of active material per plant.

Plants are treated by soaking and sprinkling with water to serve as controls.

Under these conditions, it is found on the July 24 that protection of the treated strawberry plants is complete, whereas 76% of the untreated controls are dead.

EXAMPLE 10

Pimento test

After pricking out, 10 pimento plants (Yolo wonder variety) are transplanted on the 27th June in pots of soil artificially contaminated with *Phytophtora capsici*. Immediately afterwards and then once every 8 days until the July 18, the plants are sprayed with an aqueous solution containing compound No. 2, the total application of compound No. 2 amounting to 0.5 g per plant.

Plants are sprayed with water to serve as controls.

Under these conditions, the treated plants are intact at the end of August, whereas the controls are all dead by the July 25.

All these Examples clearly demonstrate the remarkable fungicidal activity of the compounds according to the invention, on the one hand a systemic anti-mildew activity which both prevents and stops the development of fungus in the vine, and on the other hand on certain phytophtora.

However, the compounds according to the invention have also been found to be extremely effective on other types of parasitic fungi, such as: *Guignardia bidwellii* in the vine, *Pseudoperonospora humuli*, *Bremia lactucae*, *Peronospora sp.*, *Phytophtora palmivora*, *Phytophtora phaseoli*, *Phytophtora megasperma*, *Phytophtora drechsteri* and other *Phytophtora sp.* in temperate-climate or tropical-climate cultures which commonly infest such as hops, market-gardening cultures and, in particular, strawberries, capsicum, onions, sweet peppers, tomatoes, haricot beans, as well as in ornamental plants, pineapples, soya, citrus fruits, cacao trees, coconut palms, hevea.

Accordingly, the compounds according to the invention are particularly suitable for use in the preventive or curative treatment of fungus disease in plants, especially diseases of the kind caused by phycomycetes basidiomycetes, and ascomycetes in the vegetable species already referred to and, more generally, in agriculture, arboriculture, horticulture, market-gardening and, more especially, in viticulture.

The compounds according to the invention may be used with advantage in admixture with one another or with other known fungicides, such as metal dithiocarbamates (Manebe, zinebe, mancozebe), basic salts or hydroxides of copper (oxychloride, oxysulphate), (tetrahydro)phthalimides (captane, captafol, folpel), methyl N-(1-butyl carbamoyl)-2-benzimidazole carbamate (benomyl), 1,2-di-(3-methoxy or ethoxy)-2-carbonyl thioureidobenzenes (thiophanates), methyl 2-benzimidazole carbamate, etc., either to complete the range of activity of the compounds according to the invention or to increase their persistence.

It has also been found that these compounds may be mixed with other fungicidal phosphorus derivatives active against mildew, in particular with optionally substituted 2-hydroxy-1,3,2-dioxapholanes, phosphorous acid and its salts, phosphonic monoesters and their salts, as described in French Patent Applications Nos. 73-01.803, 73-37.994, 73-43.081 and 73-45.627, respectively.

The doses used may vary within wide limits according to the virulence of the fungus and the climatic conditions.

Generally, application from concentrations of from 0.01 to 5 g/l of active material are perfectly adequate.

For their practical application, the compounds according to the invention are preferably not used alone. More often they form part of formulations which generally contain a vehicle or a support and/or a surfactant in addition to the active material according to the invention. In the context of the invention, a "support" is a natural or synthetic, organic or mineral material with which the active material is associated to facilitate its application to the plant, to seeds or to soil, or its transportation or handling. The support may be solid (clays, natural or synthetic silicates, resins, waxes, solid fertilisers . . . ) or fluid (water, alcohols, ketones, petroleum fractions, chlorinated hydrocarbons, liquefied gases for aerosol propellants).

The surfactant may be an ionic or non-ionic emulsifier, dispersant or wetting agent. Examples of suitable surfactants are salts of polyacrylic acids, lignin sulphonic acids, condensates of ethylene oxide with fatty alcohols, fatty acids or fatty amines.

The compositions according to the invention may be prepared in the form of wettable powders, soluble powders, dusting powders, granulates, solutions, emulsifiable concentrates, emulsions, suspended concentrates and aerosols.

The wettable powders are normally prepared in such a way that they contain from 20 to 95% by weight of active material and normally contain, in addition to a solid support, from 0 to 5% by weight of a wetting agent, from 3 to 10% by weight of a dispersant and, where necessary, from 0 to 10% by weight of one or more stabilisers and/or other additives, such as penetration agents, adhesives or antilumping agents, colorants, etc. The composition of a wettable powder is shown by way of example below:

| | |
|---|---:|
| active material | 50 % |
| calcium lignosulphate (deflocculant) | 5 % |
| anionic wetting agent | 1 % |
| antilumping silica | 5 % |
| kaolin (filler) | 39 % |

The water-soluble powders are obtained by mixing 20 to 95% by weight of active material, 0 to 10% by weight of an antilumping filler and 0 to 1% by weight of a wetting agent, the balance being formed by a water-soluble filler, usually a salt.

One example of the composition of a water-soluble powder is given below:

| | |
|---|---:|
| active material | 70 % |
| anionic wetting agent | 0.5 % |
| antilumping silica | 5 % |
| sodium sulphate (soluble filler) | 24.5 % |

Aqueous dispersions and emulsions, for example compositions obtained by diluting with water a wettable powder or an emulsifiable concentrate according to the invention, are included within the general scope of the invention. These emulsions may be of the water-in-oil type or of the oil-in-water type and on concentrated form they may have a thick consistency resembling that of a "mayonnaise".

The compositions according to the invention may contain other ingredients, for example protective colloids, adhesives or thickeners, thixotropic agents, stabilisers or sequestrants, as well as other known pesticides, more especially acaricides or insecticides. The latter formulations are useful for controlling both the fungal disease and its insect vectors.

The term "control" as used herein is in the sense of 7 USC 135ff, 148.

The above detailed description and examples are merely illustrative of presently prefered modes of practicing the invention. All equivalents mentioned or art-recognized are intended for inclusion in the practice of this invention.

I claim:

1. Isomeric cyclic diphosphorous compounds of the following formulae:

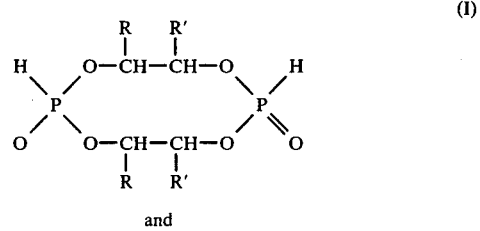

and

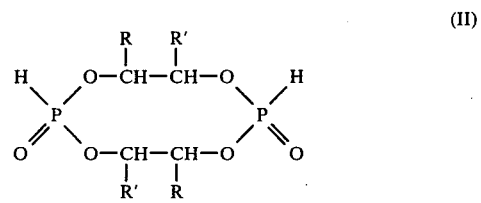

wherein
R and R' are hydrogen, but cannot both be hydrogen; alkyl radicals containing 1 to 5 carbon atoms; and halogenated alkyl radicals of 1–5 carbon atoms; and mixtures thereof.

2. The compounds as claimed in claim 1, wherein R represents hydrogen and R' is a methyl radical or halomethyl radical.

3. The compounds as claimed in claim 1, wherein the radicals R and R' are both methyl radicals.

* * * * *